(12) United States Patent
Hwang et al.

(10) Patent No.: US 9,850,187 B2
(45) Date of Patent: Dec. 26, 2017

(54) PROCESS FOR PRODUCING CUMENE

(75) Inventors: Shyh-Yuan H. Hwang, Needham, MA (US); Dana E. Johnson, Hopkinton, MA (US)

(73) Assignee: BADGER LICENSING LLC, Boston, MA (US)

( * ) Notice: Subject to any disclaimer, the term of this patent is extended or adjusted under 35 U.S.C. 154(b) by 0 days.

(21) Appl. No.: 14/409,814

(22) PCT Filed: Jun. 27, 2012

(86) PCT No.: PCT/US2012/044313
§ 371 (c)(1),
(2), (4) Date: Dec. 19, 2014

(87) PCT Pub. No.: WO2014/003732
PCT Pub. Date: Jan. 3, 2014

(65) Prior Publication Data
US 2015/0183695 A1    Jul. 2, 2015

(51) Int. Cl.
*C07C 2/66*    (2006.01)
*C07C 6/06*    (2006.01)
*C07C 6/12*    (2006.01)

(52) U.S. Cl.
CPC ............ *C07C 6/06* (2013.01); *C07C 2/66* (2013.01); *C07C 6/126* (2013.01); *C07C 2529/70* (2013.01); *Y02P 20/52* (2015.11)

(58) Field of Classification Search
CPC ..................................................... C07C 2/66
USPC ................. 585/467, 446, 450, 901
See application file for complete search history.

(56) References Cited

FOREIGN PATENT DOCUMENTS

EP    0467007 A1    1/1992

OTHER PUBLICATIONS

Office Action issued in the corresponding European Application No. 12735700.2 dated Feb. 27, 2017.
Voronina, G. A. et al: "Transformation of butyl-benzene fraction under condition of alkylation reaction", Neftepererabotka I Neftekhimija, No. 5 (Jan. 1, 1988), pp. 33-34.
Schmidt et al: "Industrial catalytic processes-phenol production", Applied Catalysis A: General, Elsevier Science, Amsterdam, NL, vol. 280, No. 1, Feb. 25, 2005 (Feb. 25, 2005), pp. 89-103, XP027814433, ISSN: 0926-860X.
Voronina, G. A. et al: "Conversion of butylbenzene fractions under alkylation conditions", Neftepererabotka I Neftekhimiya (Moscow, Russian Federation), (5), 33-4 CODEN: NNNSAF; ISSN: 0028-1190, 1988.
International Search Report and Written Opinion issued in the corresponding PCT/US2012/044313 dated Apr. 17, 2013.

*Primary Examiner* — Thuan D Dang
(74) *Attorney, Agent, or Firm* — Roberts Mlotkowski Safran Cole & Calderon P.C.

(57) ABSTRACT

A process is described for producing cumene comprising contacting benzene and a C3 alkylating agent under alkylation conditions with an alkylation catalyst in an alkylation zone to produce an alkylation effluent comprising cumene and alkylaromatic compounds heavier than cumene. Cumene is recovered from the alkylation effluent to leave a byproduct stream containing the alkylaromatic compounds heavier than cumene, which is separated into a polyisopropylbenzene-containing stream, an aromatic overhead stream, and a bottoms product. At least part of the aromatic overhead stream is recycled to the alkylation zone to reduce raw material consumption and improve cumene yield.

13 Claims, No Drawings

PROCESS FOR PRODUCING CUMENE

CROSS-REFERENCE TO RELATED APPLICATIONS

The present application is a U.S. National Phase of PCT/US2012/044313 filed on Jun. 27, 2012. The disclosure of the PCT Application is hereby incorporated by reference into the present Application.

FIELD

The present application relates to a process for producing cumene. More particularly, the present application relates to a process for improving cumene yield in a zeolite-based cumene production process.

BACKGROUND

Cumene is an important intermediate in the chemical and polymer industries. The majority of all cumene manufactured in the world today is used for the production of phenol. The demand for phenol for the manufacture of Bisphenol-A and subsequently polycarbonates is accelerating, owing to the broadening applications of polycarbonates in the electronic, healthcare, and automobile industries.

Cumene is typically produced by alkylating benzene with a $C_3$ alkylating agent, such as propylene, under liquid phase or mixed gas-liquid phase conditions in the presence of acid catalysts, particularly zeolite catalysts. In addition to cumene, the process produces diisopropylbenzene (DIPB), some triisopropylbenzene (TIPB) and other heavy by-products so it is conventional to transalkylate the polyisopropylbenzenes (PIPB) with benzene to generate additional cumene. The product of the transalkylation reaction is then fed, together with the alkylation reaction effluent, to one or more benzene columns, to recover unreacted benzene, then to one or more cumene columns, to recover the desired cumene product. The bottoms of the cumene column(s) is typically further distilled in one or more PIPB columns to recover most of the DIPB and part of the TIPB for recycle to the transalkylator. The remainder of the TIPB and essentially all of the compounds heavier than TIPB are typically discharged at the bottoms of the PIPB column as the residue. An aromatic purge is also generally taken at the overhead of PIPB column to remove excess butylbenzenes and cymenes produced in the alkylation reactor due to the presence of butene in the propylene feed and toluene in the benzene feed. This aromatic purge typically represents a yield loss of about 0.3 to 1.0%, even though the total concentration of butylbenzenes and cymenes in this aromatic purge is typically less than 10 weight %, the balance being mainly recoverable compounds such as cumene and DIPB.

It has now been found that, if at least part of the aromatic purge is recycled to the alkylation reactor, butylbenzene and cymene within the aromatic purge can be alkylated to useful cumene precursors and compounds heavier than triisopropylbenzene. The heavier compounds can be effectively removed from the system downstream of the alkylation reactor, whereas the cumene precursors can be recycled to produce additional cumene. Recoverable compounds contained within the aromatic purge, such as cumene and DIPB, are partly converted to recoverable cumene precursors in the alkylator, and fully recycled to produce additional cumene. Accordingly, an improvement in cumene process yield can be achieved.

SUMMARY

In one aspect, the invention resides in a process for producing cumene comprising contacting benzene and a $C_3$ alkylating agent under alkylation conditions with an alkylation catalyst in an alkylation zone to produce an alkylation effluent comprising cumene and alkylaromatic compounds heavier than cumene; recovering cumene from the alkylation effluent to leave a byproduct stream containing the alkylaromatic compounds heavier than cumene; separating the byproduct stream containing said alkylaromatic compounds heavier than cumene into a polyisopropylbenzene-containing stream, an aromatic overhead stream, and a bottoms stream; and recycling at least part of the aromatic overhead stream to the alkylation zone.

In one embodiment, the polyisopropylbenzene-containing stream is contacted with benzene in the presence of a transalkylation catalyst in a transalkylation zone to produce a transalkylation effluent comprising additional cumene. The additional cumene can then be recovered from the transalkylation effluent, generally after the transalkylation effluent has been combined with the alkylation effluent.

Generally, the aromatic overhead stream comprises from 0.1 to 40 weight %, such as from 0.2 to 20 weight %, of the byproduct stream.

Typically, the aromatic overhead stream comprises butylbenzene and cymene in a total concentration of up to 50 weight %, such as from 0.1 to 30 weight %.

DETAILED DESCRIPTION

Described herein is a process for producing cumene by the alkylation of benzene with a $C_3$ alkylating agent, particularly propylene, isopropanol, or their mixture, in the presence of an alkylation catalyst in an alkylation zone. In addition to unreacted benzene and the desired cumene product, the alkylation reaction effluent comprises various alkylaromatic compounds heavier than cumene, particularly diisopropylbenzene (DIPB) and triisopropylbenzene (TIPB) as well as certain additional byproducts resulting from reaction of impurities in the benzene and $C_3$ alkylating agent feeds. Typical of such byproducts are butylbenzenes and cymenes. Butylbenzenes and cymenes are typically removed from the system through an aromatic overhead stream at the PIPB column. The aromatic overhead stream typically contains less than 10 weight % of butylbenzenes and cymenes, the balance being mainly recoverable compounds such as cumene and DIPB. Such a purge typically represents an overall cumene yield loss of about 0.3 to 1.0%. In the present process, instead of purging the entire aromatic overhead stream, at least part of the aromatic overhead stream is recycled to the alkylation reactor to produce cumene precursor compounds which can be converted to additional cumene product and thereby improve the overall cumene yield.

The alkylation reaction is typically conducted at a temperature of about 20° C. to about 350° C., for example about 50° C. to about 300° C., such as about 100° C. to about 280° C., and a pressure of about 100 kPa to about 20,000 kPa, for example about 500 kPa to about 10,000 kPa, so that at least part of the reaction mixture is maintained in the liquid phase during the process. Generally, the molar ratio of benzene to the $C_3$ alkylating agent is maintained within the range of about 1:1 to about 30:1, typically from 1.1:1 to 10:1. Although any $C_3$ alkylating agent can be used for the alkylation step, the present process has particular application where the $C_3$ alkylating agent is propylene, isopropanol, or their mixture.

The catalyst employed in the alkylation reaction generally comprises at least one molecular sieve of the MCM-22 family. As used herein, the term "molecular sieve of the MCM-22 family" (or "material of the MCM-22 family" or "MCM-22 family material" or "MCM-22 family zeolite") includes one or more of:

- molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);
- molecular sieves made from a common second degree building block, being a 2-dimensional tiling of such MWW framework topology unit cells, forming a monolayer of one unit cell thickness, preferably one c-unit cell thickness;
- molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and
- molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof.

In addition to or instead of the MCM-22 family material, the alkylation catalyst may comprise at least one medium pore molecular sieve having a Constraint Index of 2-12 (as defined in U.S. Pat. No. 4,016,218). Suitable medium pore molecular sieves include ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

Alternatively, the alkylation catalyst may comprise one or more large molecular sieves having a Constraint Index less than 2 in addition to the MCM-22 family material. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. Nos. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

The above molecular sieves may be used as the alkylation catalyst without any binder or matrix, i.e., in so-called self-bound form. Alternatively, the molecular sieve may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 weight % and more usually, particularly, when the composite is prepared in the form of beads, in the range of about 2 to about 80 weight % of the composite.

The alkylation reaction may be carried out batchwise or on a continuous basis. Moreover, the reaction may be carried out in a fixed or moving bed. Fixed bed operation is, however, preferred, typically with the alkylation reaction zone comprising one or a plurality of series-connected beds of alkylation catalysts.

The effluent of the alkylation reaction comprises unreacted benzene, cumene product and a variety of byproducts resulting from unwanted reactions which inherently compete with the desired monoalkylation of the benzene with the $C_3$ alkylating agent. These byproducts mainly comprise polyalkylated species, especially diisopropylbenzene (DIPB), some triisopropylbenzene (TIPB), but also include heavy ($C_{15+}$) aromatic compounds and products resulting from reaction of impurities present in the commercial benzene feed and the $C_3$ alkylating agent. For example, butene is a significant impurity in commercial propylene and can react with benzene during the alkylation reaction to produce butylbenzenes, especially tert-butylbenzene and sec-butylbenzene. Similarly, toluene is present in most benzene feedstocks and can react with $C_3$ alkylating agent during the alkylation reaction to produce cymenes, such as p-cymene (4-isopropyltoluene).

The effluent of the alkylation reaction is fed to one or more benzene distillation columns, where the unreacted benzene is recovered as an overhead stream for recycle to the alkylation reactor and/or a transalkylation reactor (as described below). The bottoms from the benzene column(s) are then fed to one or more cumene distillation columns to recover the desired cumene product. The bottoms from the cumene column(s) contain the majority of the $C_{10+}$ byproducts of the alkylation reaction and are fed to one or more PIPB distillation columns to separate a PIPB stream containing most of the DIPB and part of the TIPB for passage to the transalkylation reactor. The remainder of the TIPB and essentially all of the compounds heavier than TIPB are discharged at the bottoms of the PIPB column as residue. In addition, a $C_{12}$-overhead stream is withdrawn from the PIPB column and, rather than being entirely purged from the system, is at least partly recycled to the alkylation reactor. In particular, as illustrated by the Examples, it has been found that unrecoverable compounds in this overhead stream, such as butylbenzene and cymene, react in the alkylation reactor partly to produce compounds heavier than TIPB and partly to produce $C_{15}$-cumene precursor compounds, such as sec-butylcumenes, tert-butylcumenes and methyl-diisopropyl-benzenes. These cumene precursor compounds are recovered from the alkylation effluent by the PIPB distillation column(s) as part of the DIPB-containing stream and are recycled to the transalkylation reactor, where they react with benzene to produce additional cumene. The recoverable compounds in the overhead stream, such as cumene and DIPB, are partly converted to cumene precursors and fully recycled to produce additional cumene.

Typically, the aromatic overhead stream comprises from 0.1 to 40 weight %, typically from 0.2 to 20 weight % of the byproduct stream rejected as bottoms by the cumene column (s) and fed to PIPB column(s). Where the $C_3$ alkylating agent is propylene, isopropanol, or their mixture, the aromatic overhead stream comprises butylbenzene and cymene in a total concentration of up to 50 weight %, typically from 0.1 to 30 weight %.

The transalkylation reaction is conducted in a separate reactor from the alkylation reaction and involves reacting the PIPB stream with additional benzene in the presence of a transalkylation catalyst. The transalkylation catalyst preferably comprises a molecular sieve selected from MCM-22, PSH-3, SSZ-25, MCM-36, MCM-49, MCM-56 and zeolite beta. In addition, the transalkylation catalyst may comprise ZSM-5, zeolite X, zeolite Y, or mordenite, such as TEA-mordenite. The transalkylation catalyst may be the same as or different from the alkylation catalyst. Suitable transalkylation conditions include a temperature of 50° C. to 300° C., a pressure of 100 KPa to 20,000 KPa, a weight hourly space velocity of 0.2 to 20 on total feed and benzene/PIPB weight ratio 0.5:1 to 10:1.

As used herein, the term "$C_n$" hydrocarbon wherein n is a positive integer, e.g., 1, 2, 3, 4, 5, 6, 7, 8, 9, 10, 11, 12, means a hydrocarbon having n number of carbon atom(s) per molecule. The term "$C_n+$" hydrocarbon wherein n is a positive integer, e.g., 1, 2, 3, 4, 5, 6, 7, 8, 9, 10, 11, 12, as used herein, means a hydrocarbon having at least n number of carbon atom(s) per molecule. The term "$C_n-$" hydrocarbon wherein n is a positive integer, e.g., 1, 2, 3, 4, 5, 6, 7, 8, 9, 10, 11, 12, as used herein, means a hydrocarbon having no more than n number of carbon atom(s) per molecule.

The following examples are merely illustrative and intended to be non-limiting.

Example 1

Alkylation of benzene with propylene was carried out in a fixed bed reactor, made from a ¾ inch (19 mm) diameter Schedule 40 Stainless Steel 316 pipe with a total length of 34 inches (864 mm). A storage tank was used for benzene and another tank was used for propylene. A positive displacement pump was used for feeding the benzene feed into the reactor and another positive displacement pump was used for feeding propylene into the reactor. The flow rates of the benzene feed and propylene were set by pump settings and monitored by electronic weight scales. The reactor operating conditions were controlled and monitored by an automatic control system. A portion of the reactor effluent was circulated back to the reactor inlet by a centrifugal pump to control the temperature rise across the catalyst bed. The feedstock and reactor effluent were analyzed by three Hewlett Packard 5890 Series II Gas Chromatographs, the first one equipped with a Chrompack CP-Wax 52CB column having an inside diameter of 0.25 mm, film thickness of 0.5 µm, and length of 60 meters, the second one equipped with an Agilent DB-1 column having an inside diameter of 0.32 mm, film thickness of 0.5 µm, and length of 60 meters, and the third one equipped with an Agilent HP-PONA column having an inside diameter of 0.20 mm, film thickness of 0.5 µm, and length of 50 meters.

43 grams of an MCM-22 family catalyst was loaded into the fixed bed reactor. The reactor was heated up in pure benzene and the catalyst dried out at 150° C. The reactor temperature was then lowered to 128° C. before the propylene feed was introduced. The propylene feed weight hourly space velocity (WHSV) was 0.7 $hr^{-1}$, the feed benzene to propylene ratio was 2:1 molar, and the reactor inlet temperature was 128° C. The reactor circulation was adjusted to control the temperature rise across the catalyst bed below 30° C. The catalyst performance was stable.

The pure benzene feed was then switched to a feed containing 99% benzene and 1% tert-butylbenzene for four days during which period the catalyst performance remained stable. The analysis of the reactor effluent sample indicated that the tert-butylbenzene conversion was 27% with the following selectivity:

12% to iso-butane;
73% to tert-butylcumenes; and
15% to compounds heavier than TIPB.

The iso-butane produced can be easily purged out of the system as part of the benzene column overhead vent gas. The compounds heavier than TIPB can be effectively purged out of the system at the PIPB column bottoms as part of the residues due to their high boiling points. The tert-butylcumenes can be recovered as part of the recycle PIPB stream and recycled back to the transalkylator with benzene, where they can react with benzene to form cumene and tert-butylbenzene. The additional cumene made can be recovered by distillation in the cumene column as part of the desired cumene product and the tert-butylbenzene can be recovered at the PIPB column overhead and recycled back to alkylator until it goes to extinction.

Example 2

The same reactor setup and catalyst loading described in Example 1 were used in this Example. A feed containing 99% benzene and 1% sec-butylbenzene was used for three days during which period the catalyst performance remained stable. The analysis of the reactor effluent sample indicated that the sec-butylbenzene conversion was 16% with the following selectivity:

91% to sec-butylcumenes; and
9% to compounds heavier than TIPB.

The compounds heavier than TIPB can be effectively purged out of the system at the PIPB column bottoms as part of the residues due to their high boiling points. The sec-butylcumenes can be recovered as part of the recycle PIPB stream and recycled back to the transalkylator with benzene, where they can react with benzene to form cumene and sec-butylbenzene. The additional cumene can be recovered by distillation in the cumene column as part of the desired cumene product and the sec-butylbenzene can be recovered at the PIPB column overhead and recycled back to alkylator until it goes to extinction.

Example 3

The same reactor setup and catalyst loading described in Example 1 were used in this example. A feed containing 99% benzene and 1% para-cymene was used for four days during which period the catalyst performance remained stable. The analysis of the reactor effluent sample indicates that the para-cymene conversion was 20% with the following selectivity:

87% to methyl-DIPB; and
13% to compounds heavier than TIPB

The compounds heavier than TIPB can be effectively purged out of the system at the PIPB column bottoms as part of the residues due to their high boiling points. The methyl-D1PB can be recovered as part of the recycle PIPB stream and recycled back to the transalkylator with benzene, where they can react with benzene to form cumene and para-cymene. The additional cumene made can be recovered by distillation in the cumene column as part of the desired cumene product and the para-cymene can be recovered at the PIPB column overhead and recycled back to alkylator until it goes to extinction.

The experimental results described above therefore indicate that the efficiency of commercial cumene production process can be improved by recycling at least part of the PIPB column overhead aromatic purge to the alkylation reactor.

While various embodiments have been described, it is to be understood that variations and modifications may be resorted to as will be apparent to those skilled in the art. Such variations and modifications are to be considered within the purview and scope of the claims appended hereto.

The invention claimed is:

1. A process for producing cumene, the process comprising:
   (a) contacting benzene and a $C_3$ alkylating agent under alkylation conditions with an alkylation catalyst in an alkylation zone to produce an alkylation effluent comprising cumene and alkylaromatic compounds heavier than cumene, wherein said alkylation catalyst comprises at least one zeolite catalyst selected from the group consisting of ZSM-3, ZSM-4, ZSM-5, ZSM-11, ZSM-12, ZSM-14, ZSM-18, ZSM-20, ZSM-22, ZSM-23, ZSM-35, ZSM-48, zeolite beta, zeolite Y, Ultrastable Y (USY), Dealuminized Y (Deal Y), mordenite, MCM-22, PSH-3, SSZ-25, ERB-1, ITQ-1, ITQ-2, MCM-36, MCM-49, MCM-56, and UZM-8;
   (b) recovering cumene from said alkylation effluent to leave a byproduct stream containing said alkylaromatic compounds heavier than cumene;
   (c) separating the byproduct stream into a polyisopropylbenzene-containing stream, an aromatic overhead stream, and a bottoms stream; and
   (d) recycling at least part of the aromatic overhead stream to the alkylation zone, wherein aromatic overhead stream comprises butylbenzene and/or cymene in a total concentration of up to 50 weight % to form cumene precursors.

2. The process of claim 1 and further comprising:
   (e) contacting the polyisopropylbenzene-containing stream with benzene in the presence of a transalkylation catalyst in a transalkylation zone to produce a transalkylation effluent comprising cumene.

3. The process of claim 2 and further comprising:
   (f) recovering cumene from the transalkylation effluent.

4. The process of claim 3, wherein the alkylation effluent and the transalkylation effluent are combined before recovering cumene from the effluents.

5. The process of claim 1, wherein the aromatic overhead stream comprises from 0.1 to 40 weight % of the byproduct stream.

6. The process of claim 1, wherein butylbenzene in the overhead stream is alkylated to produce butylcumenes and one or more compounds heavier than triisopropylbenzene in the alkylation zone.

7. The process of claim 1, wherein cymene in the overhead stream is alkylated to produce methyl-diisopropylbenzenes and one or more compounds heavier than triisopropylbenzene in the alkylation zone.

8. The process of claim 1, wherein the recovering (b) comprises distillation in one or more distillation columns.

9. The process of claim 1, wherein the separating (c) comprises distillation in one or more distillation columns.

10. The process of claim 3, wherein the recovering (f) comprises distillation in one or more distillation columns.

11. The process of claim 1 and further comprising:
    (g) recovering unreacted benzene from the alkylation effluent and recycling the unreacted benzene to the alkylation zone.

12. The process of claim 3 and further comprising:
    (h) recovering unreacted benzene from the alkylation effluent and transalkylation effluent and recycling the unreacted benzene to at least one of the alkylation zone and the transalkylation zone.

13. The process of claim 1, wherein:
    the alkylation effluent comprises cumene, diisopropylbenzene and triisopropylbenzene;
    the polyisopropylbenzene-containing stream comprises diisopropylbenzene and triisopropylbenzene;
    the aromatic overhead stream comprises cumene, butylbenzene, and cymene; and
    the bottoms product comprises triisopropylbenzene and compounds heavier than triisopropylbenzene.

* * * * *